United States Patent [19]

Wiktor

[11] Patent Number: 4,886,062
[45] Date of Patent: Dec. 12, 1989

[54] INTRAVASCULAR RADIALLY EXPANDABLE STENT AND METHOD OF IMPLANT

[75] Inventor: Dominik M. Wiktor, Cranford, N.J.

[73] Assignee: Medtronic, Inc., Minneapolis, Minn.

[21] Appl. No.: 109,686

[22] Filed: Oct. 19, 1987

[51] Int. Cl.$^4$ .............................................. A61M 29/02
[52] U.S. Cl. ........................................ 128/343; 623/1; 267/180
[58] Field of Search .......... 128/325, 341–345, 128/348.1; 604/53, 104–106; 623/1, 13; 267/180, 182, 165, 166; 285/15; 138/97, 172; 24/129 C, 131 R, 131 C

[56] References Cited

U.S. PATENT DOCUMENTS

| 4,503,569 | 3/1985 | Dotter | 128/325 |
| 4,553,545 | 11/1985 | Maass et al. | 128/341 |
| 4,580,568 | 4/1986 | Gianturco | 128/345 |
| 4,649,922 | 3/1987 | Wiktor | 128/344 |
| 4,665,918 | 5/1987 | Garza et al. | 128/343 |
| 4,733,665 | 3/1988 | Palmaz | 128/343 |
| 4,739,762 | 4/1988 | Palmaz | 128/343 |
| 4,760,849 | 8/1988 | Kropf | 604/104 |
| 4,768,507 | 9/1988 | Fischell et al. | 128/341 |
| 4,800,882 | 1/1989 | Gianturco | 128/343 |
| 4,830,003 | 5/1989 | Wolff et al. | 128/343 |

FOREIGN PATENT DOCUMENTS 837122  4/1952  Fed. Rep. of Germany ...... 267/180

Primary Examiner—Stephen C. Pellegrino
Assistant Examiner—Ralph Lewis
Attorney, Agent, or Firm—Robert J. Klepinski; Joseph F. Breimayer

[57] ABSTRACT

A device to be used as a vascular stent comprising a cylindrical open-ended wire component made of a low memory metal such as copper alloy, titanium, or gold, providing a radial support from within a blood vessel after implantation therein. The coronary stent is characterized by its ability to be expanded radially to a larger diameter after initial implantation and means for causing said stent to expand to a larger diameter and a method for transporting, positioning and implantation of such coronary stent transluminarely to have said stent act as a permanent prosthesis to assure vascular patency. And method for simultaneous angioplasty and stent implant procedure.

13 Claims, 2 Drawing Sheets

INTRAVASCULAR RADIALLY EXPANDABLE STENT AND METHOD OF IMPLANT

FIELD OF THE INVENTION

This invention relates to intravascular implants for maintaining vascular patency in humans and animals. The present invention comprises an open-ended wire formed device of basically cylindrical shape and made of a softer-then spring type metal and fitted over an inflatable element of a typical balloon type catheter such as described in U.S. Pat. No. 4,195,637 and U.S. Pat. No. 4,402,307. The wire formed device is intended to act as a permanent prosthesis stent and is implanted transluminarely. Specifically this invention is characterized by the ability of said intravascular stent to be enlarged radially after having been introduced percutaneously, transported transluminarely and positioned at desired location. In addition, this invention relates to a method whereby a permanent prosthesis stent is implanted at the same time the angioplasty procedure is being performed. This invention is particularly useful in transluminar implantation of a stent in the field of cardiology and especially in the case of coronary angioplasty to prevent restenosis.

BACKGROUND OF THE INVENTION

In my U.S. Pat. No. 4,649,992 a device is described in combination with a catheter which is basically a compression spring retained between a partially inflated balloon and an abuttment immediately behind the balloon on the catheter shaft. The intent is to transport the spring prosthesis in this manner to the desired location and then after a successful angioplasty procedure release said spring prosthesis by totally evacuating said balloon, thus allowing said spring prosthesis to expand linearely and stay in place while the balloon catheter is withdrawn. This method is quite simple and its simplicity is very attractive; however it has some drawbacks. One an and foremost is the fact that the spring has a fixed diameter and as such is unable to fully conform to the inside wall of the vessel which at times is quite tortuous and thus could conceivably create a somewhat turbulant flow of blood, and possible thrombosis could in some cases result. Other Patents, eg. U.S. Pat. No. 4,553,545 teaches a different method where a relatively complex mechanical rotating device and co-axial cables are employed to achieve the necessary means to change the diameter of the implanted stent to a larger dimension at the point if implant. Still other Patents, eg. U.S. Pat. No. 3,868,956 describes a method wherein a temperature responsive metallic device is used and expanded after implant using external heat sources. All of the above mentioned devices present drawbacks of various magnitudes including blood coagulation and possible thrombosis, and considerable complexity of procedure.

In angioplasty procedures at this time, in many cases restenosis occures soon thereafter, which requires a secondary procedure or a surgical bypass operation. The implanted prosthesis as described herein will preclude such additional procedures and will maintain vascular patency indefinately.

Depending on the size used, the stent according to this invention can also be efficacious in other similar applications, such as: Repairs of aneurysms, support of artificial vessels or liners of vessels, innitial repairs of dissections and mechanical support to prevent collapsing of dialated vessels. Still many other and similar applications will be satisfied by this invention without departing from the basic premise and concept.

This stent and the method of its use particularely allows a single procedure to combine the essential angioplasty and a simultaneous implant of a permanent prosthesis designed and intended to prevent restenosis and further complications arising therefrom, also reducing the risk factor and trauma for the patient.

Other reference publications:
1. Self-expanding metalic stents for small vessels Radiology 1987—162.469-472.
2. Flexible Balloon-expandable stent for small vessels Radiology January 87.
3. Intravascular stents to prevent occlusion and restenosis after transluminar angioplasty, N.E.J. of M. Mar. 19 1987.
4. U.S. Pat. No. 4,580,568 Percutaneous endovascular stent.
5. U.S. Pat. No. 4,503,569 Transluminarely placed expandable graft prosthesis, Dotter 1985.
6. U.S. Pat. No. 4,649,992 Catheter arrangement having a variable diameter tip and spring prosthesis, Wiktor 1987
7. U.S. Pat. No. 4,681,110 Catheter arrangement and blood vessel liner, Wiktor 1987

All of the above references describe and teach various methods of providing or otherwise offering and introducing stents of different types and designs for applications similar to the one described herein in this invention.

SUMMARY OF THE INVENTION

The improvement of this invention over other similar devices such as sited in patents above, and specifically my previous invention described in U.S. Pat. No. 4,649,992, is the ability of the device of this invention to allow for and to maintain a very low profile and a small frontal area, so very important for purposes of percutaneous insertion. Thus the stent of this invention can be inserted into and be transported via a standard #8F Guiding Catheter such as USCI Cat.# 006128, while using standard procedures and methods. Once on location, the stent can be expanded radially to a diameter larger then initially introduced; a ratio of=2½:1 can easily be achieved with a wire diameter of 0.008 and initial stent diameter of 0.075. The expanded larger diameter will conform to the inside of the vessel and maintain intimate contact with the inside wall. The stent of this invention is characterized by the low memory level of the relatively easily deformable metal used for the wire.

The configuration of stent 1, shown in FIG. 1, is such, that the wire 2 is initially preformed into a two-dimensional zig-zag form 3, basically creating a flat expandable band 3a. The zig-zag pattern can vary as to its shape and tightness of the reversing bends, but for reasons of simple description a typical sinusoidal form is chosen to depict this band's construction.

In order to create the stent 1, and to have it assume an initial configuration as shown in FIG. 1, also a subsequently radially expanded condition as shown in FIG. 5, a length of preformed band 3a is wrapped on a suitable mandrel 4 in a manner similar to that of winding a simple helical spring again as shown in FIG. 1. Care is taken to form the wire band 3a flat around the mandrel 4 with little or no tension to prevent premature linear expansion of band 3a.

Once the zig-zag band 3a is wound into a cylindrical shape, it is removed from the mandrel 4, and is placed over a suitable variable diameter device such as an inflatable balloon 5 typically used for angioplasty procedures as shown in FIG. 2. A suitable forming tool (not shown) is used to tighten the stent over the balloon; manual operation of squeezing the stent over the balloon is also acceptable.

A controlled radial expansion of the stent is accomplished by the force generated by the inflating balloon. When acted upon by the the inflating balloon, the stent of this invention being characterized by the zig-zag preformed wire band 3a subsequently formed into an open-ended cylindrical shape, is by design and intent capable to expand radially.

The radial expansion in effect is achieved by controlled deformation and tension applied to the sinusoidal pattern of the preformed wire band 3a. The low memory metal used for the fabrication of the wire formed stent assures, that the radially expanded stent stays expanded thus fulfilling its primary intent and function. Other advantages of this invention over those mentioned earlier Ref. 1 through 7, are the inherent post-expansion radial rigidity and linear flexibility an excellent combination for an intravascular and especially intracoronary stent. In the case of intracoronary application an overriding factor being the ability of allowing for an extremely low profile and a very small frontal area so very essential for initial transluminar introduction and transportation through a standard 8F guiding catheter.

A major object of this invention is the provision of a preformed flexible wire stent which allows easy radial expansion and subsequent retention of the radially expanded shape well anchored within a vessel.

Still another object of this invention is the simplicity of its application, especially with respect to angioplasty, where one procedure accomplishes two distinct functions: In combination with the balloon it compresses the plaque, thus creating a recannalized lumen as characterized by angioplasty, and deploys and implants a permanent prosthesis within the newly created and recannalized lumen to prevent possible reclosure and restenosis thus allowing free flow of blood indefinately. Both functions are performed simultaneously and with a single insertion of the catheter.

DESCRIPTION OF THE PREFERRED EMBODIMENT

For purposes of better and clearer understanding of this invention reference is made to FIGS. 1-6. The preferred embodiment of this invention is shown and described in an application for angioplasty; however, it is understood that other applications not specifically mentioned herein are possible and no limitations in scope of this invention are intended or implied without departing from the basic principles of this invention.

Figure 1:
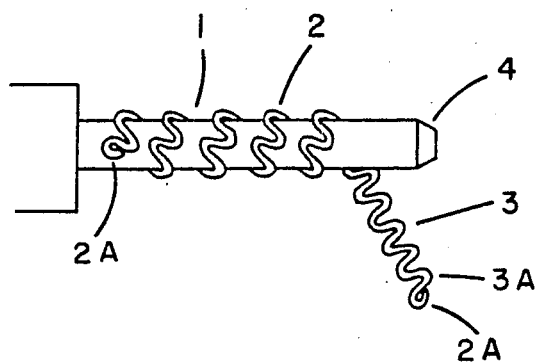
FIG. 1 is a side elevation of a preferred embodiment of a stent according to this invention being wound on a mandrel.

FIG. 1 shows the details of construction of the prosthesis stent 1, hereafter called stent, which is basically of a hollow open-ended cylindrical shape. Stent 1 is basically a tubular shape of coiled preformed wire band typically wound on a suitable mandrel 4. The wire is made of drawn low-memory level material such as stainless steel, titanium ASTM F63-83 Grade 1 or high carat gold K 19–22. Copper alloy typically 110 when properly coated with polyester or Teflon can also be used. Titanium and gold are biologically compatible and inert and require no special treatment.

Figure 2:
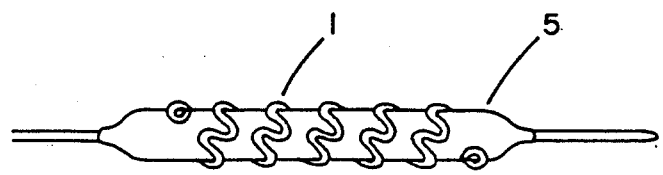
FIG. 2 is a side elevation showing an overall view of a stent prosthesis fitted over a deflated balloon.
Figure 5:
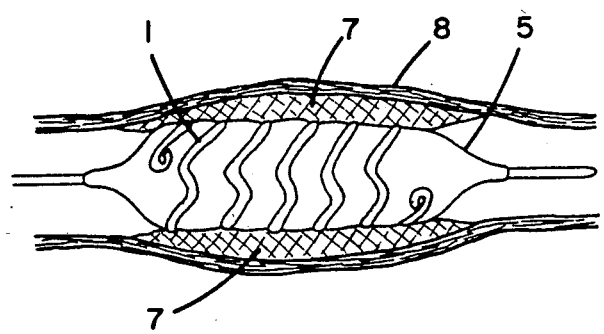
FIG. 5 is similar to FIG. 4, the balloon inflated, and the stent radially expanded, illustrating the preferred method of an angioplasty procedure coupled with a simultaneous deployment and implantation of a permanent prosthesis stent.
Figure 6:
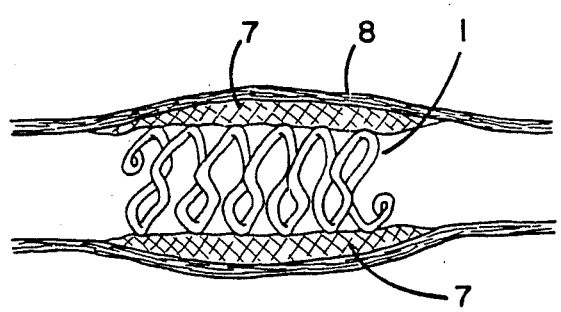
FIG. 6 is a view similar to FIG. 5 showing the prosthesis stent implanted and plaque compressed and retained after removal of the balloon.

In FIG. 2 it is shown that the stent 1 is centrally located and positioned with respect to the length of balloon 5 and that flat preformend wire band 3a turns are evenly spaced so that when stent 1 is expanded as shown in FIG. 5 and FIG. 6, stent 1 will provide even support inside vessel 8, and be able to resist external loading.

Figure 3:
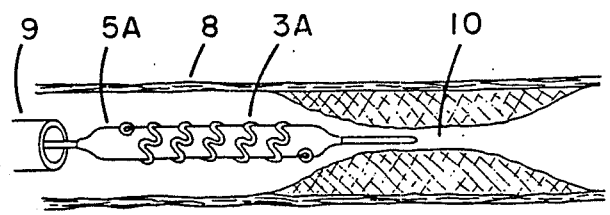
FIG. 3 shows the balloon and stent assembly advanced within a vessel, approaching a partial occlusion.
Figure 4:
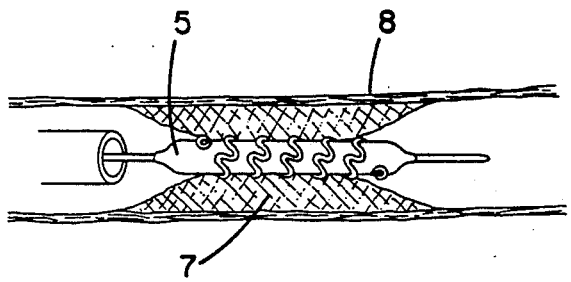
FIG. 4 is similar to FIG. 3 showing the balloon and stent assembly inside a partially occluded vessel.

In FIG. 3 it is shown how balloon and stent assembly 5a emanate from guiding catheter 9 inside vessel 8 and is advanced towards partial occlusion 10. In FIG. 4 it is shown how balloon and stent assembly 5a are located inside occlusion 10 within artery 8, balloon 5 still being deflated. Once positively placed within occlusion 10, balloon 5 is inflated using standard angioplasty procedures and techniques. As balloon 5 expands, so does the stent 1 as shown in FIG. 5. The expanding balloon 5 together with stent 1 compresses the plaque 7, said plaque remains compressed and stent 1 retains said plaque 7 and prevents possible reocclusion. Angioplasty procedure completed, balloon 5 is deflated and withdrawn leaving stent 1 firmly implanted within vessel 8. Previously occluded vessel 8 is now completely recannalized and patency is restored.

FIG. 6 shows stent 1 firmly implanted and imbedded in compressed plaque 7, providing both adequate support as well as a smooth lumen void of all protrusions, a very desireable feature and condition, since any protrusions are conducive to turbulant blood flow and potential formation of thrombosis.

To test the viability of this novel principle of stent construction a polyester-coated copper wire of 0.008 dia. was preformed into a zig-zag pattern 3 as shown in FIG. 1 to form a band 3a. This band was subsequently wound into a tubular shape with ends curled into tight loops 2a to prevent sharp ends of wire 2 from perforating balloon 5. The tubular stent was placed over a 3.5 mm PTCA 20/3.5T balloon made by SciMed and fitted tightly over said balloon. The balloon and stent assembly was fed through an 8F guiding catheter into a silastic thin-wall tubing approx 3 mm inside diameter and balloon was inflated with a standard 10 cc syringe using plain water. The expansion of the stent was observed and documented on video. Several subsequent tests of similar nature also using larger balloons typically MeadoxSurgimed A/S Cat. No. 700720 10 mm dia. and Medi.tech balloon 12 mm dia. were used with a stent made of polyester-coated copper wire 0.014" dia. All tests showed near-perfect expansion and "bench-type" implantations. Further experiments showed that multiple stents can be used in tandem. In fact, a typical balloon and stent assembly can be fed right through a previously implanted and expanded stent and be implanted downstream ahead of the previously implanted stent. A distinct advantage in real life situations.

Experimental laboratory tests on animals are now being conducted. initial results are very encouraging and promising. Both intracoronary and intraaortic stents are being investigated at this time, a complete protocol is being prepared.

Five stents recently implanted in small arteries of pigs and expanded to 3.5 mm have successfully maintained 100% patency for several weeks and as of this date continue to do so.

In a separate experiment, a previously created aortic dissection has been stopped by expanding a 10 mm diameter stent within said dissection.

I claim:

1. A radially expandable stent for implantation within a body vessel, comprising
   a wire formed winding in a hollow cylindrical shape,
   the winding including a preformed zig-zag type pattern continuous wire formed flat band,
   the flat band wound into a continuous helix the length of the stent, and
   a full loop terminating both ends of zig-zag preformed wire band.

2. A stent as defined in claim 1 wherein the unexpanded stent has an outside diameter less then 0.075 inch.

3. A stent as defined in claim 2 wherein the stent is radially expandable to approximately three times its original diameter.

4. A stent as defined in claim 1 in combination with means within the wire winding for expanding the winding.

5. A radially-expandable stent for implantation within a body vessel comprising:
   a stent body having a wall of generally cylindrical shape formed of a helical coil made of a wire, the body having a longitudinal axis and a first diameter;
   zig-zag means in the wire for allowing radial expansion of the cylindrical stent body from the first diameter to a second larger diameter without significantly altering body length along the longitudinal axis.

6. The stent of claim 5 wherein the zig-zag pattern is a generally sinusoidal bend in the wire.

7. The stent of claim 6 wherein the sinusoidal bend lies generally within the cylindrical shape of the stent wall.

8. The stent of claim 5 wherein the wire has an end formed in a loop.

9. A method of forming a radially-expandable stent for implantation within a body vessel comprising:
   bending a wire in a zig-zag pattern; and
   winding the wire around a form in a coil.

10. The method of claim 9 wherein the step of bending includes forming the zig-zag pattern in the wire generally in a plane and the step of winding the wire includes winding with the zig-zag pattern flat against the form.

11. The method of claim 9 further comprising:
    forming a loop in an end of the wire.

12. A method of forming a radially-expandable stent for implantation within a body vessel comprising:
    forming a wire into a sinusoidal shape;
    forming the wire into a coil having a first diameter and a first longitudinal length, so that later radial outward deformation of the cylinder to a second larger diameter does not significantly alter the longitudinal length.

13. A stent for implantation within a body vessel comprising:
    a cylindrical stent body formed of a continwous wire, the stent body having a first diameter and a first length along a longitudinal axis, the wire lying generally at an acute angle to a line through the cylindrical body parallel to the longitudinal axis; and
    zig-zag means in the wire for allowing radial outward expansion of the body without significantly altering the length of the body.

* * * * *

UNITED STATES PATENT AND TRADEMARK OFFICE

(12)            CERTIFICATE EXTENDING PATENT TERM
UNDER 35 U.S.C. § 156

| | | | |
|---|---|---|---|
| (68) | PATENT NO. | : | 4,886,062 |
| (45) | ISSUED | : | December 12, 1989 |
| (75) | INVENTOR | : | Dominik M. Wiktor |
| (73) | PATENT OWNER | : | Medtronic, Inc. |
| (95) | PRODUCT | : | Wiktor® Prime Coronary Stent System |

This is to certify that an application under 35 U.S.C. § 156 has been filed in the United States Patent and Trademark Office, requesting extension of the term of U.S. Patent No. 4,886,062 based upon the regulatory review of the product Wiktor® Prime Coronary Stent System by the Food and Drug Administration. Since it appears that the requirements of the law have been met, this certificate extends the term of the patent for the period of

(94)                 1,347 days from October 19, 2007, the original expiration date of the patent, subject to the payment of maintenance fees as provided by law, with all rights pertaining thereto as provided by 35 U.S.C. § 156(b).

I have caused the seal of the Patent and Trademark Office to be affixed this 18th day of July 2001.

Nicholas P. Godici
Acting Under Secretary of Commerce for Intellectual Property and
Acting Director of the United States Patent and Trademark Office